US00PP21739P2

(12) United States Plant Patent
McLean et al.

(10) Patent No.: US PP21,739 P2
(45) Date of Patent: Mar. 1, 2011

(54) ***SYZYGIUM* PLANT NAMED 'BIG RED'**

(50) Latin Name: *Syzygium australe*
Varietal Denomination: Big Red

(76) Inventors: Peta McLean, Queensland (AU); Scott McLean, Queensland (AU)

( * ) Notice: Subject to any disclaimer, the term of this patent is extended or adjusted under 35 U.S.C. 154(b) by 5 days.

(21) Appl. No.: 12/462,087

(22) Filed: Jul. 29, 2009

(51) Int. Cl.
*A01H 5/00* (2006.01)

(52) U.S. Cl. ..... Plt./226

(58) Field of Classification Search ..... Plt./226
See application file for complete search history.

(56) References Cited

PUBLICATIONS

UPOV ROM GTITM Computer Database GTI Jouve Retrieval Software 2010/;03 Citation for 'Big Red'.*
Anonymous. *Syzugium* 'big Red'. Plants Management Australia available at: http://www.pma.com.au/fact_files/s%20big%20red%20fact%20sheet.pdf accessed Sep. 27, 2010.*

* cited by examiner

*Primary Examiner*—Wendy C. Haas
(74) *Attorney, Agent, or Firm*—C. A. Whealy

(57) ABSTRACT

A new and distinct cultivar of *Syzygium* plant named 'Big Red', characterized by its upright to bushy to outwardly spreading plant habit; relatively large leaves that are initially greyed orange in color; developing stems are greyed purple in color; and good garden performance.

3 Drawing Sheets

Botanical designation: *Syzygium australe.*
Cultivar denomination: 'BIG RED'.

BACKGROUND OF THE INVENTION

The present invention relates to a new and distinct cultivar of *Syzygium* plant, botanically known as *Syzygium australe,* and hereinafter referred to by the name 'Big Red'.

The new *Syzygium* plant originated from an open-pollination in 2003 in Clagiraba, Queensland, Australia, of *Syzygium australe* 'Aussie Compact', not patented, as the female, or seed, parent with an unknown selection of *Syzygium australe,* as the male, or pollen, parent. The new *Syzygium* was discovered and selected by the Inventor as a single plant within the progeny of the stated open-pollination in a controlled nursery environment in Clagiraba, Queensland, Australia in 2004.

Asexual reproduction of the new *Syzygium* plant by cuttings in Clagiraba, Queensland, Australia since 2004, has shown that the unique features of this new *Syzygium* plant are stable and reproduced true to type in successive generations.

SUMMARY OF THE INVENTION

Plants of the new *Syzygium* have not been observed under all possible environmental conditions. The phenotype may vary somewhat with variations in environment such as temperature and light intensity, without, however, any variance in genotype.

The following traits have been repeatedly observed and are determined to be the unique characteristics of 'Big Red'. These characteristics in combination distinguish 'Big Red' as a new and distinct cultivar of *Syzygium:*

1. Upright to bushy to outwardly spreading plant habit.
2. Relatively large leaves that are initially greyed orange in color.
3. Developing stems are greyed purple in color.
4. Good garden performance.

Plants of the new *Syzygium* differ from plants of the female parent, 'Aussie Compact', in the following characteristics:

1. Plants of the new *Syzygium* are taller and have longer internodes than plants of 'Aussie Compact'.
2. Plants of the new *Syzygium* have larger leaves than plants of 'Aussie Compact'.
3. Developing leaves and stems of plants of the new *Syzygium* are greyed orange and purple, respectively, in color whereas developing leaves and stems of plants of 'Aussie Compact' are yellow green in color.

Plants of the new *Syzygium* can also be compared to plants of the *Syzygium australe* 'Elegance', not patented. Plants of the new *Syzygium* differ primarily from plants of 'Elegance' in the following characteristics:

1. Plants of the new *Syzygium* are taller and broader than plants of 'Elegance'.
2. Plants of the new *Syzygium* have broader leaves than plants of 'Elegance'.
3. Developing leaves and stems of plants of the new *Syzygium* are greyed orange and purple, respectively, in color whereas developing leaves and stems of plants of 'Elegance' are brown in color.

BRIEF DESCRIPTION OF THE PHOTOGRAPHS

The accompanying photographs illustrate the overall appearance of the new *Syzygium* plant. The photographs show the colors as true as it is reasonably possible to obtain in colored reproductions of this type. Colors in the photographs may differ slightly from the color values cited in the detailed botanical description which accurately describe the colors of the new *Syzygium* plant.

The photograph on the first sheet comprises a side perspective view of typical plants of 'Big Red' grown in an outdoor nursery.

The photograph on the second sheet is a side perspective view of a typical plant of 'Big Red' grown in a container.

The photograph on the third sheet is a close-up view of a typical plant of 'Big Red'.

DETAILED BOTANICAL DESCRIPTION

The aforementioned photographs and following observations and measurements describe plants grown in Clagiraba, Queensland, Australia during the summer and autumn in 30-cm containers in an outdoor nursery and under conditions and practices which approximate those generally used in commercial *Syzygium* production. During the production of the plants, day temperatures ranged from 33° C. to 40° C. and night temperatures ranged from 22° C. to 23° C. Measurements and numerical values for represent averages for typical 13-month old plants. In the following description, color references are made to The Royal Horticultural Society Colour Chart, 2007 Edition, except where general terms of ordinary dictionary significance are used.

Botanical classification: *Syzygium australe* 'Big Red'.

Parentage:

*Female, or seed, parent.*—*Syzygium australe* 'Aussie Compact', not patented.

*Male, or pollen, parent.*—Unknown selection of *Syzygium australe,* not patented.

Propagation:

*Type.*—By cuttings.

*Time to initiate roots, summer.*—About seven to ten days at 20° C. to 25° C.

*Time to initiate roots, winter.*—About 10 to 14 days at 15° C. to 20° C.

*Time to produce a rooted young plant, summer.*—About 25 to 30 days at 20° C. to 25° C.

*Time to produce a rooted young plant, winter.*—About 35 to 40 days at 15° C. to 20° C.

*Root description.*—Medium in thickness; fibrous; white in color.

*Rooting habit.*—Moderately branching; sparse to moderately dense.

Plant description:

*Plant form/growth habit.*—Evergreen perennial; upright to bushy to outwardly spreading plant habit; inverted triangle; relatively medium to tall and medium in width; vigorous growth habit.

*Plant height at maturity.*—About 4 meters.

*Plant diameter or spread at maturity.*—About 2.5 meters.

*Stem description.*—Branching habit: Freely branching habit, plants are dense and bushy. Internode length: About 3 cm to 4.8 cm. Aspect: About 40° to 45° from vertical. Strength: Strong. Texture: Smooth, glabrous. Color, developing: Close to 187A. Color, mature: Close to 199C.

Foliage description:

*Arrangement.*—Opposite and alternate, simple.

*Attitude.*—Horizontal to semi-erect.

*Length.*—About 6 cm to 7 cm.

*Width.*—About 3.8 cm to 4.5 cm.

*Shape.*—Elliptic.

*Apex.*—Abruptly acute; outwardly hooked.

*Base.*—Obtuse and slightly asymmetric.

*Margin.*—Entire; undulation absent to very weak.

*Texture, upper and lower surfaces.*—Smooth, glabrous.

*Venation pattern.*—Pinnate.

*Color.*—Newly emerged leaves, upper and lower surfaces: Between 166A and 177A. Developing leaves, upper surface: Between 146A to 148A; towards the margins, close to 174A. Developing leaves, lower surface: Close to 148A. Fully expanded leaves, upper surface: Close to N137A; midrib, close to 151A; lateral venation, close to N137A. Fully expanded leaves, lower surface: Close to 147B; midrib, close to 151A; lateral venation, close to 147B.

*Petioles.*—Length: About 4.7 mm to 5.3 mm. Color: Immature, upper and lower surfaces: Close to 178A. Developing, upper and lower surfaces: Close to 177B. Fully developed, upper and lower surfaces: Close to 146B.

Flower description: Flower development has not been observed to date on plants of the new *Syzygium.*

Disease/pest resistance: Plants of the new *Syzygium* have not been shown to be resistant to pathogens and pests common to *Syzygium.*

Garden performance: Plants of the new *Syzygium* have been observed to have good garden performance and to tolerate wind, rain, drought and high temperatures of about 40° C.

It is claimed:

1. A new and distinct *Syzygium* plant named 'Big Red' as illustrated and described.

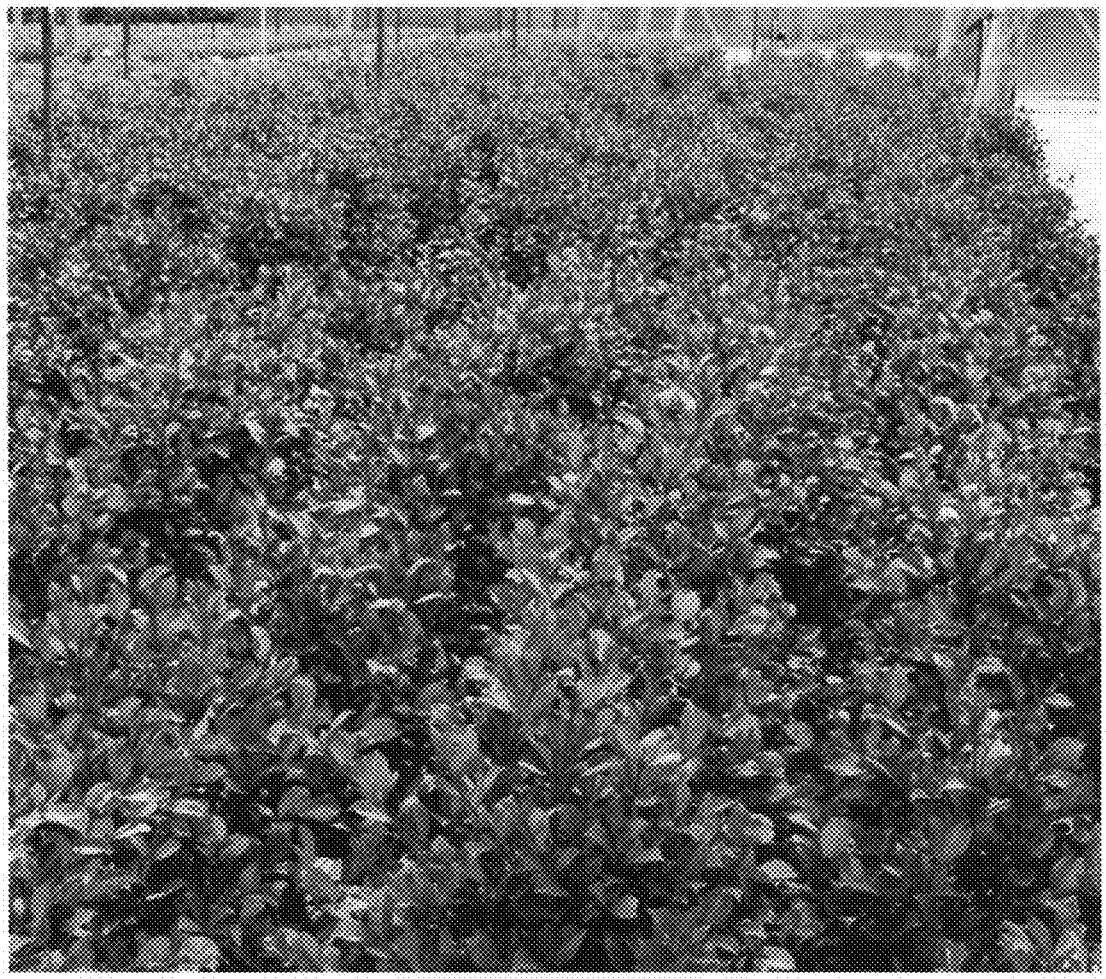

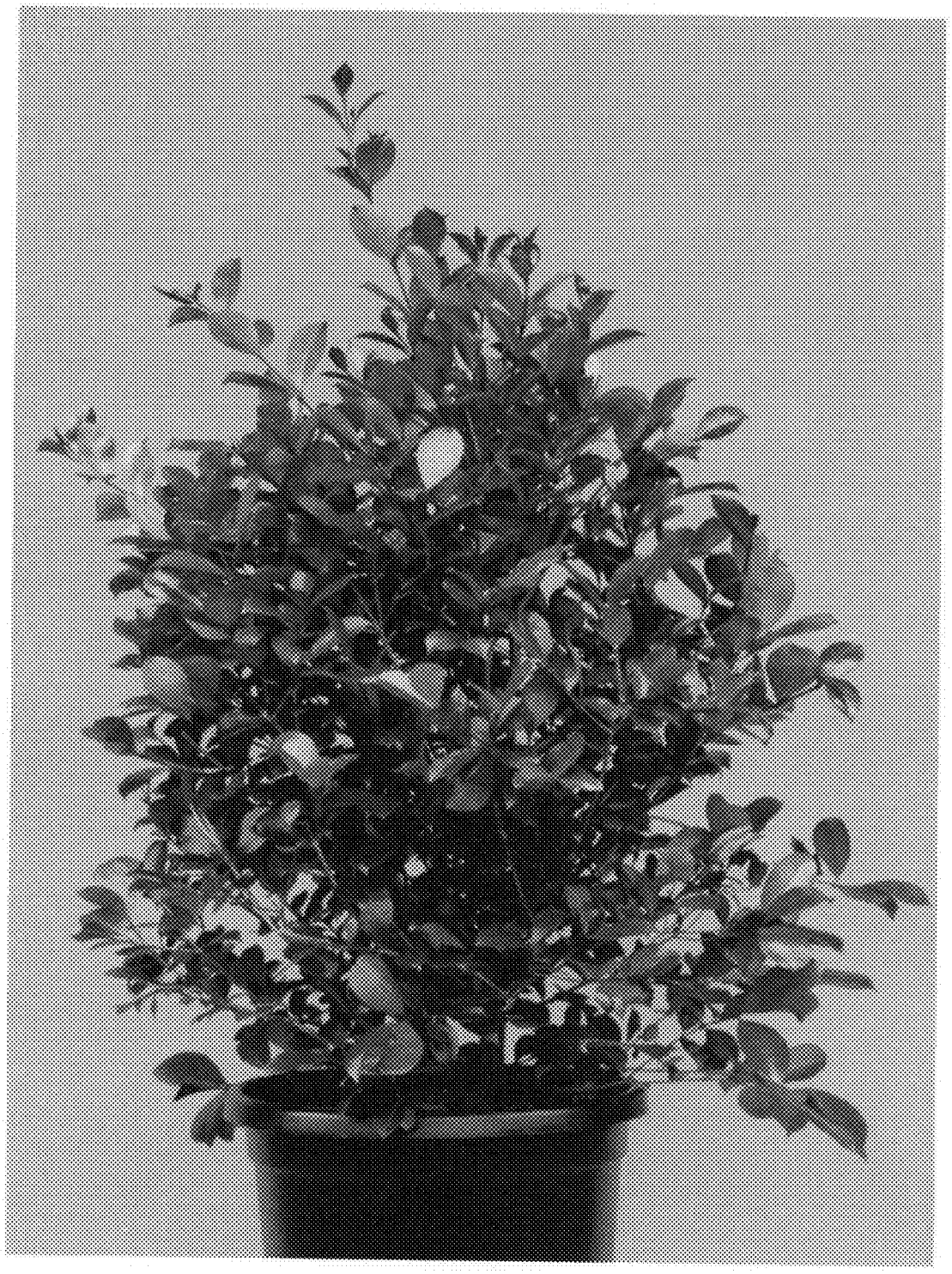

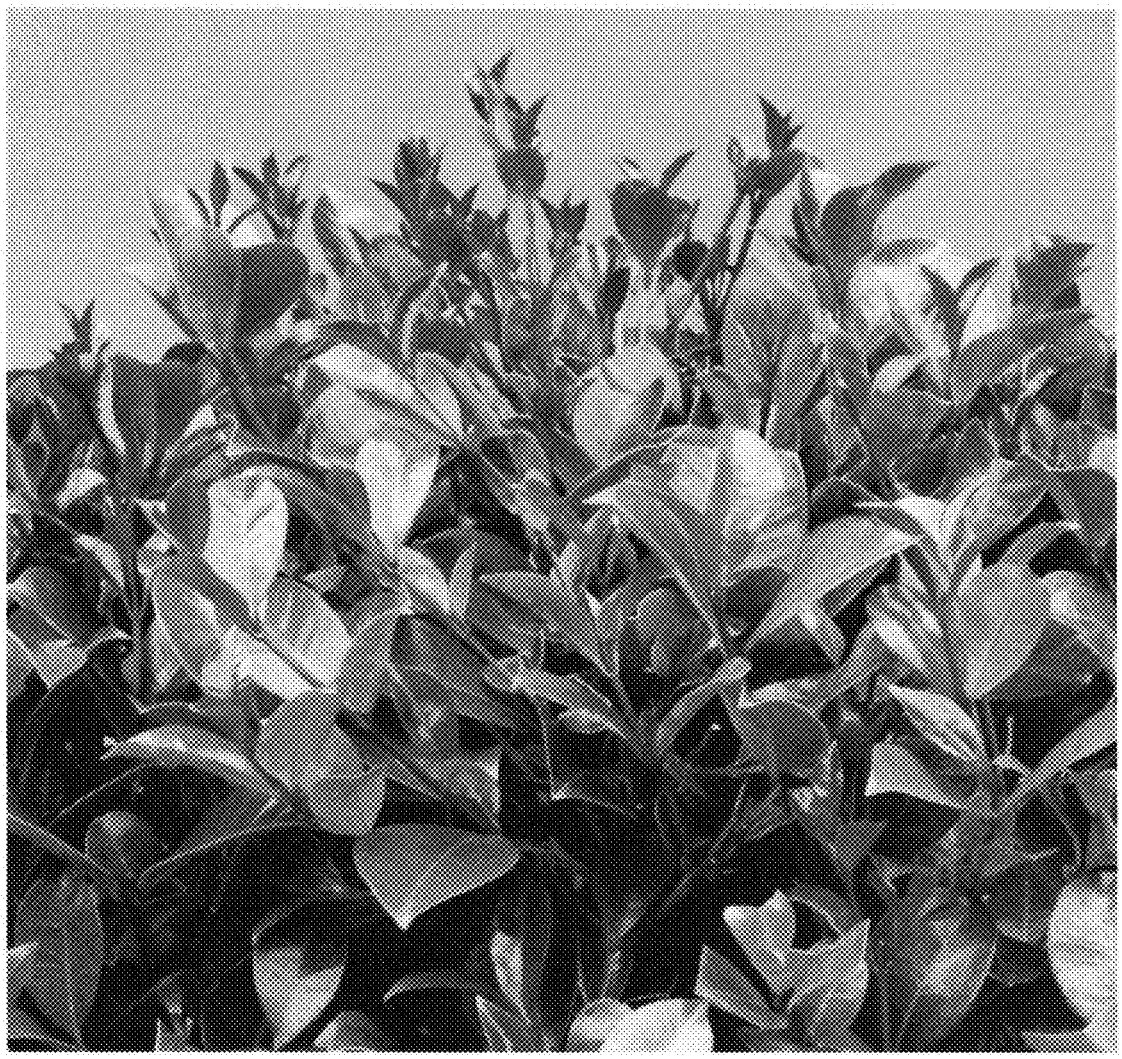

* * * * *